United States Patent [19]
Corace

[11] Patent Number: 5,814,011
[45] Date of Patent: Sep. 29, 1998

[54] ACTIVE INTRAVASCULAR LUNG

[75] Inventor: Russell A. Corace, Grand Rapids Township, Mich.

[73] Assignee: Medtronic, Inc., Minneapolis, Minn.

[21] Appl. No.: 638,019

[22] Filed: Apr. 25, 1996

[51] Int. Cl.⁶ .................................................. A61M 37/00
[52] U.S. Cl. .............................. 604/23; 604/26; 604/151; 604/155
[58] Field of Search ................................... 604/151, 155, 604/52, 53, 23, 5, 26

[56] References Cited

U.S. PATENT DOCUMENTS

| | | |
|---|---|---|
| 4,583,969 | 4/1986 | Mortensen . |
| 4,625,712 | 12/1986 | Wampler . |
| 4,632,107 | 12/1986 | Butler . |
| 4,704,121 | 11/1987 | Moise . |
| 4,753,221 | 6/1988 | Kensey et al. . |
| 4,779,614 | 10/1988 | Moise . |
| 4,817,586 | 4/1989 | Wampler . |
| 4,846,152 | 7/1989 | Wampler et al. . |
| 4,895,557 | 1/1990 | Moise et al. . |
| 4,906,229 | 3/1990 | Wampler . |
| 4,908,012 | 3/1990 | Moise et al. . |
| 4,944,722 | 7/1990 | Carriker et al. . |
| 5,037,383 | 8/1991 | Vaslef et al. . |
| 5,061,256 | 10/1991 | Wampler . |
| 5,092,844 | 3/1992 | Schwartz et al. . |
| 5,219,326 | 6/1993 | Hattler ........................................ 604/26 |
| 5,308,314 | 5/1994 | Fukui et al. ................................. 604/4 |
| 5,336,164 | 8/1994 | Snider et al. . |
| 5,393,207 | 2/1995 | Maher et al. . |

FOREIGN PATENT DOCUMENTS

| | | |
|---|---|---|
| 0569319 A2 | 11/1993 | European Pat. Off. . |
| 0697221A1 | 2/1996 | European Pat. Off. . |
| 0 480 101 B1 | 5/1996 | European Pat. Off. . |
| PCT/US88/ 04295 | 12/1988 | WIPO . |
| WO92/17118 | 10/1992 | WIPO . |

OTHER PUBLICATIONS

PCT/ISA/220 —Notification of Transmittal of International Search Report, Jul. 25, 1997.

"Marked Enhancement of $CO_2$. . . ," by T. Nguyen et al., ASAIO, Abstracts of 39th Annual Meeting Apr. 29, 30 and May 1, 1993, p. 66.

"Current Progress in the Development . . . ," by G. Reeder et al., ASAIO, Abstracts of 39th Annual Meeting, Apr. 29, 30 and May 1, 1993, p. 68.

"A Pumping Intravascular Artificial . . . ," by A.J. Makarewicz, ASAIO, Abstracts of 39th Annual Meeting, Apr. 29, 30 and May 1, 1993, p. 68.

"A Novel Method for Measuring . . . ," by L. Lund et al., ASAIO Journal, vol. 42, No. 2, Mar.–Apr. 1996, p. 67.

"Development of Intravascular Pumping . . . ," by T. Sueda et al., ASAIO Journal, vol. 42, No. 2, Mar.–Apr. 1996, p. 68.

"Acute In Vivo Studies of the Pittsburg . . . ," by M. Macha, ASAIO Journal, vol. 42, No. 2, Mar.–Apr. 1996, p. 69.

"Recent Progress in Engineering the Pittsburgh . . . ," by W. Federspiel et al., ASAIO Journal, vol. 42, No. 2, Mar.–Apr. 1996, p. 71.

"Flow Characteristics of the Flow Field in . . . ," by H. Li et al., ASAIO Journal, vol. 42, No. 2, Mar.–Apr. 1996, p. 71.

*Primary Examiner*—Michael Powell Buiz
*Assistant Examiner*—Julian W. Woo
*Attorney, Agent, or Firm*—Foley & Lardner

[57] ABSTRACT

An active intravascular lung includes a gas exchanger for delivering oxygen to blood flowing across the gas exchanger when positioned within the cavity and a pump in proximity to the gas exchanger for creating a differential blood pressure across the gas exchanger. When the gas exchanger is positioned percutaneously in the blood flow cavity, oxygen can be delivered to the blood independent of the operation of the patient's heart.

21 Claims, 3 Drawing Sheets

ACTIVE INTRAVASCULAR LUNG

BACKGROUND OF THE INVENTION

1. Field of the Invention

The present invention relates generally to artificial lungs and, more particularly, to an active fluid flow intravascular lung for use in patients with both heart and lung ailments.

2. Description of the Related Art

Prior art lung assist devices have attempted to supply oxygen and remove carbon dioxide from patients suffering from acute illnesses such as pneumonitis, atelectasis, various heart and circulatory ailments, fluid in the lungs, obstruction of pulmonary ventilation, or lung injury caused by heat, noxious gases, or other factors. Prior techniques for assisting the lungs under these conditions have included, among others, the use of intravascular lung assist devices. With these types of devices, there is no need for anticoagulants, lung resection or constant supervision by teams of specialized technicians, as in heart-lung machines. The skin and circulation need only be violated at one site, which may lessen the risk of infection.

Despite their advantages, intravascular lung assist devices typically have a relatively poor oxygen transfer rate to the blood, which is below the ideal rate, due to convection, diffusion, blood flow rate across the intravascular lung, and oxygen saturation of the input blood. Even if the convective and diffusive limitations were eliminated, the maximum oxygen transfer would still be limited by the blood flow rate and the oxygen saturation of the input blood. A patient's blood flow rate is determined solely by how well the heart functions. When a patient suffers from both heart and lung ailments, the problem of sufficient oxygen transfer to the blood from intravascular lung assist devices is further augmented. Prior art intravascular lungs are passive and depend solely upon the blood flow rate generated by the patient.

SUMMARY OF THE INVENTION

These and other problems of the prior art are overcome by the provision of an active intravascular lung assist device configured for percutaneous venous insertion into a patient. According to one aspect of the invention, the device includes a gas exchanger for delivering oxygen to blood flowing across the gas exchanger when positioned within the cavity and a pump in proximity to the gas exchanger for creating a differential blood pressure across the gas exchanger. Thus, when the gas exchanger is positioned in the blood flow cavity, oxygen can be delivered to the blood independent of the operation of the patient's heart.

According to a further aspect of the invention, a catheter extends between the gas exchanger and the pump to control the direction, velocity, and pressure of blood flow through the gas exchanger. In another aspect, the pump is driven by a flexible drive cable that is adapted to extend and be driven extracorporeally when the pump and gas exchanger are positioned in the blood flow cavity.

In one embodiment, the pump is located at a distal end of the device and is inserted into the cavity ahead of the gas exchanger to pull blood through the gas exchanger. The flexible drive cable extends through the gas exchanger and catheter to drive the pump.

In a second embodiment, the gas exchanger is located at a distal end of the device and is inserted into the cavity ahead of the pump, so that blood is pushed through the gas exchanger.

BRIEF DESCRIPTION OF THE DRAWINGS

The invention will now be described with reference to the drawings in which.

DETAILED DESCRIPTION OF THE PREFERRED EMBODIMENTS

Figure 1:
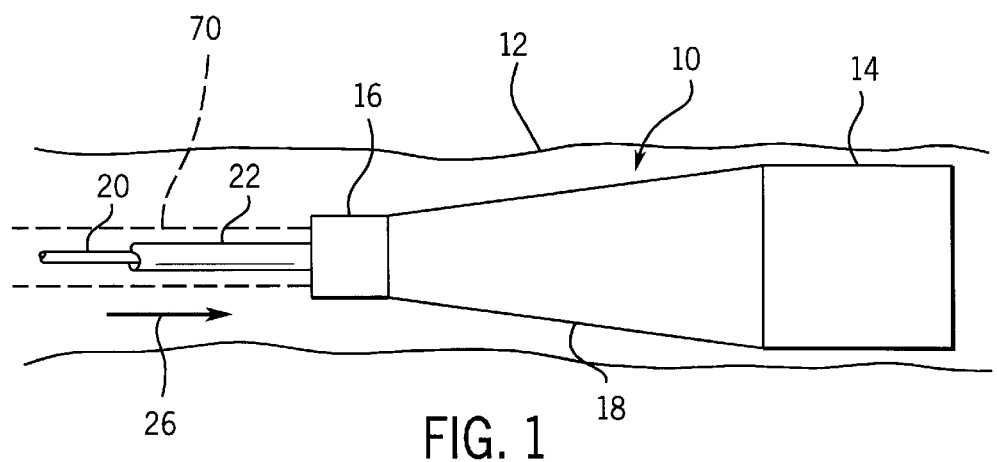
FIG. 1 is a schematic view of an active intravascular lung assist device positioned within a vein according to a first embodiment of the invention.

Referring now to FIG. 1, an active intravascular lung assist device 10 according to the present invention is positioned within a patient's vein 12. The device 10 preferably includes an intravascular membrane lung 14 connected to an active blood pump 16 via a catheter 18. The structure of the membrane lung is conventional such as that disclosed in U.S. Pat. No. 5,336,164 to Snider et al., the disclosure of which is hereby incorporated by reference. In the membrane lung shown in the Snider et al. patent, a large number of microporous fibers are tethered at one end to a manifold sleeve. The fibers are in communication with the lumina of a catheter to transfer oxygen to the blood and remove carbon dioxide therefrom. One or a plurality of such manifold sleeves may be incorporated into the active intravascular device 10 of the present invention.

Figure 4:
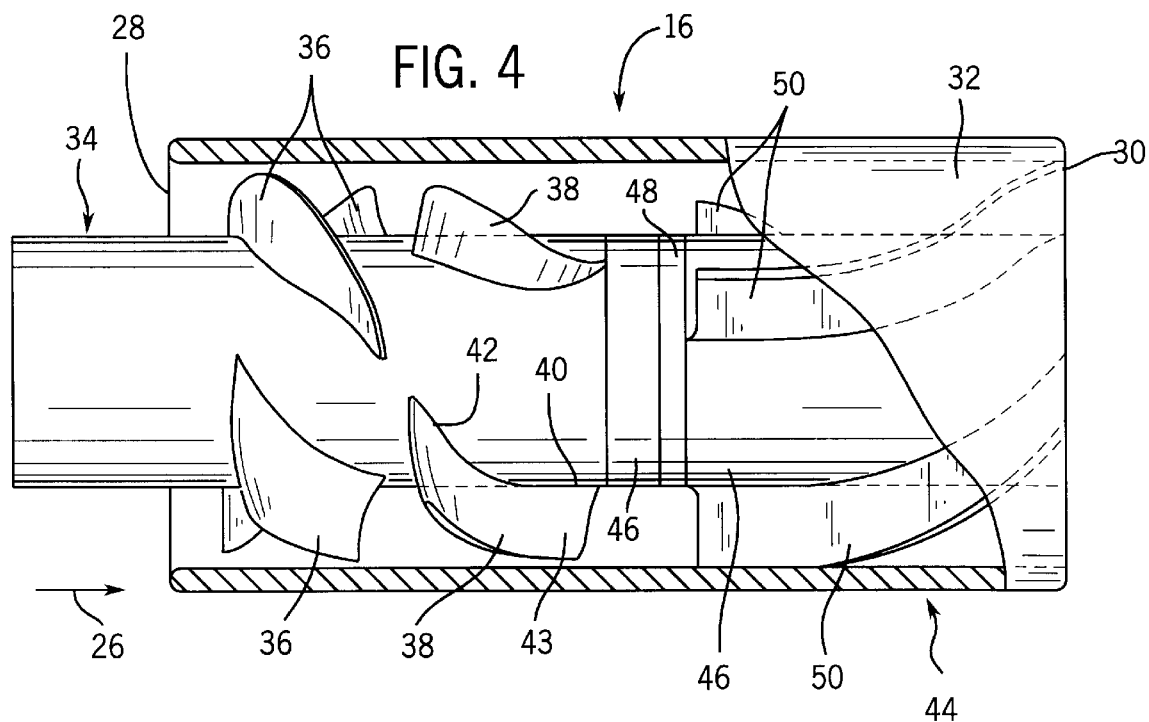
FIG. 4 is a partially broken away side view of a blood pump according to the present invention.

Referring now to FIG. 4, a miniature high-speed intravascular single stage blood pump 16 is shown. The pump comprises an outer housing 32 having a rotor 34 rotatably mounted at one end thereof and a stator 44 fixedly mounted at the other end thereof. A journal bearing 46 separates the stator 44 and rotor 34.

Blood enters the pump 16, in the direction of arrow 26, by passing around rotor 34 at the pump inlet end 28 provided at one end of an outer housing 32. The blood is rotated by the rotor 34 and forced through the housing 32, past the fixed stator 44, and ultimately, is exhausted at the pump outlet end 30 provided at the other end of the housing 32. In the embodiment shown in FIG. 4, the rotor 34 is provided with two rows of blades 36, 38. In the preferred embodiment, only a single row of blades 36 is provided on the rotor 34. Each row preferably consists of three blades spaced 120 degrees apart which wrap helically around at least a portion of the rotor body. The helical orientation of the first row of blades 36 produce a component of axial acceleration of the blood from the left to the right as shown in FIG. 4. The trailing edge of the second row of blades 38 is slightly S-shaped to form a negative angle 40 at the base of the trailing edge adjacent the rotor 34 and a positive angle 43 at the tip of the trailing edge spaced furthest away from the rotor 34. The blades 38 also have a high leading edge twist 42. This arrangement maintains a uniform velocity of the blood flow along the trailing edge of each blade 38 in order to prevent any turbulence which might cause hemolysis or separation and causes the blood to flow only along an axial component of acceleration. It also provides an increased pressure rise necessary for enabling this stage to meet its operating criteria. The high twist is necessary to overcome the viscous losses in the low Reynolds range in which blood pumps of this size operate.

The stator 44 of the pump 16 includes a journal bearing 46, and a bearing block 48. Three reverse-twisted blades 50 provided on the stator 44 and are substantially longer than the rotor blades 36 and 38. The stator blades 50 form the support for the housing 32 spacing the housing from the stator and rotor bodies.

Figure 2:
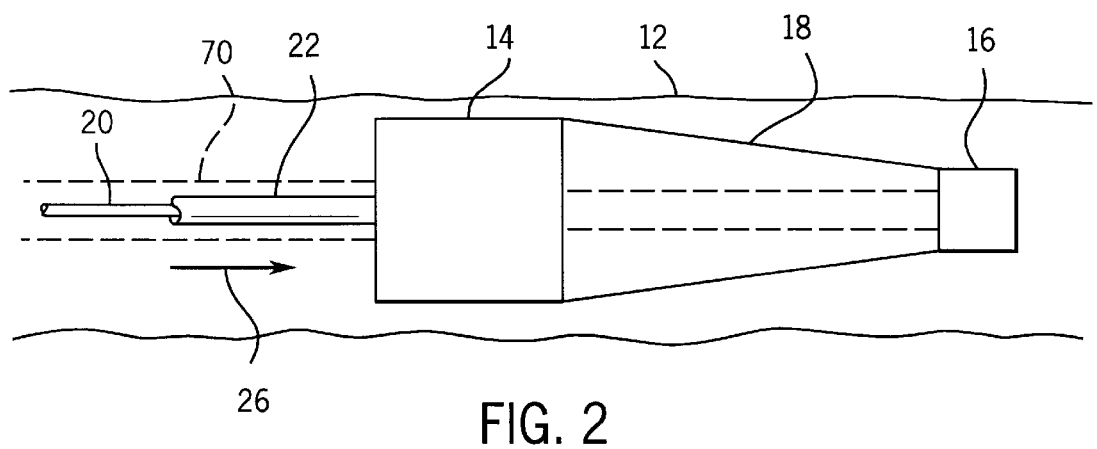
FIG. 2 is a schematic view of an active intravascular lung assist device positioned withing a vein according to a second embodiment of the invention.

Referring again to FIG. 1, the pump 16 is driven by a cable 20 encased in a sheath 22 that preferably has an outer layer formed of a soft, blood compatible material and an inner layer formed of a stiff, abrasion-resistant material. The stiff inner layer faces the cable 20 that drives the pump 16. Operation of this type of pump is described in greater detail in U.S. Pat. No. 4,846,152 to Wampler et al., the disclosure of which is hereby incorporated by reference. The pump 16 may be mounted upstream from the membrane lung 14 as shown in FIG. 1 or may be mounted downstream from the membrane lung 14 as shown in FIG. 2. In the case of FIG. 2, the sheath 22 and cable 20 extend through membrane lung 14 and catheter 18 to pump 16. The outer sheath layer is in direct contact with the blood and therefore must be formed of the blood compatible material. Although a single stage pump is preferred due to its relatively smaller size, expense, and reduction of hemolysis, dual stage blood pumps may also be used.

Figure 3:
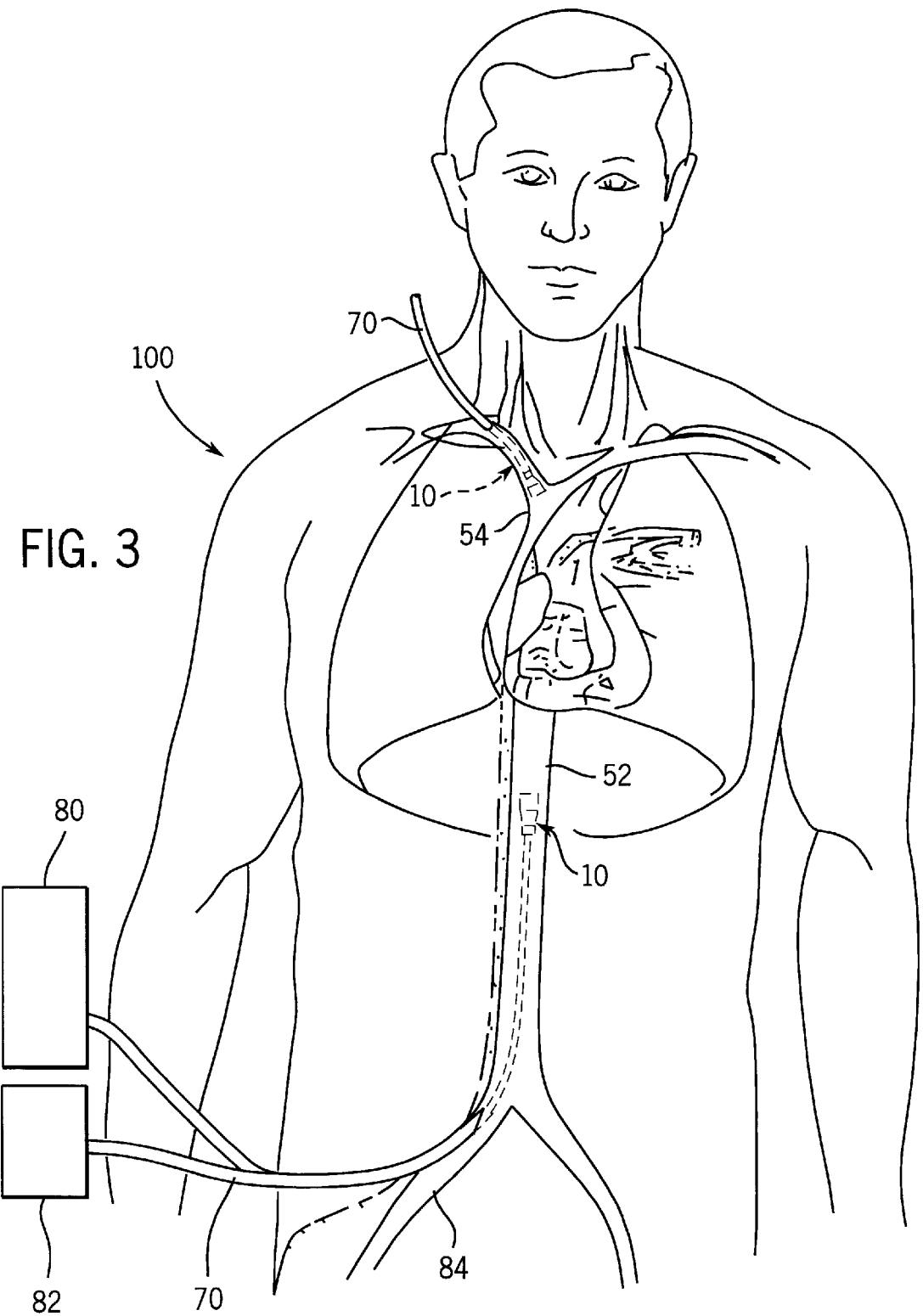
FIG. 3 is a top view of a patient having an active intravascular lung assist device placed in the inferior and superior vena cavae.

Referring now to FIG. 3, the active intravascular lung assembly 10 shown in dashed line is preferably positioned within the inferior vena cava 52 of a patient 100. An oxygenator 80 for membrane lung 14 and drive mechanism 82 for blood pump 16 are provided at the proximal end of a catheter 70. A suitable drive mechanism for powering intravascular blood pumps is disclosed in U.S. Pat. No. 4,895,557 to Moise et al., the disclosure of which is hereby incorporated by reference.

Figure 5:
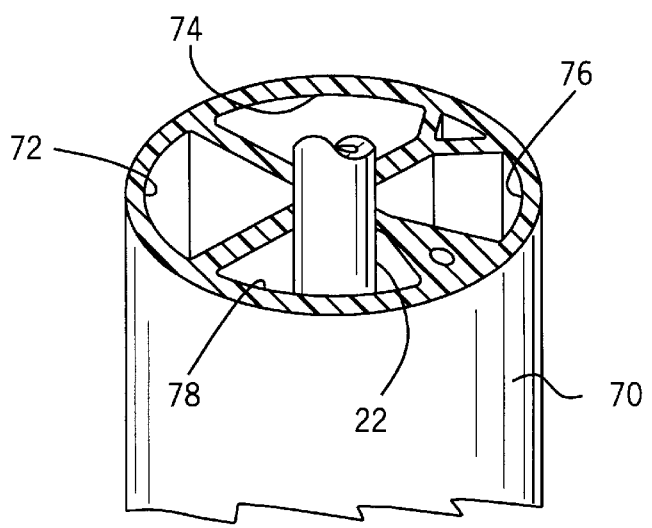
FIG. 5 is a perspective view of a catheter for use with the present invention.

Turning now to FIG. 5, a commercially available diagnostic pulmonary artery catheter 70 such as the OPTI-CATH™ catheter manufactured and sold by Oximetrix, Inc. of Mountain View, Calif. is illustrated. This catheter 70 is formed of a flexible plastic material, preferably extruded polyvinyl chloride. Specifically, it is formed to include a ventilation, or gas inlet conduit 72, a ventilation or gas outlet conduit 74, a blood sampling conduit 76, and a cable drive conduit 78. The catheter 70 may be of any suitable length and size appropriate to accommodate the gas exchange requirements of the patient.

The active intravascular lung assist device 10 of the present invention is intended to be inserted and removed percutaneously without the need for surgery. The device 10 can be positioned in the inferior vena cava 52 via the femoral vein 84 or iliac vein, preferably by the well-known Seldinger technique as described in U.S. Pat. No. 5,487,727 referenced above. Alternatively, the device 10 can be inserted into the superior vena cava 54 through the jugular vein or brachial vein. In still another embodiment, one intravascular lung device 10 can be positioned in the superior and one in the inferior vena cava depending upon the oxygenating needs of the patient.

In use, the intravascular lung assist device 10 is positioned within a vein carrying oxygen depleted blood such as the vena cava and the pump is operated to create a pressure differential across the intravascular lung from 1 to 100 mm Hg depending on the patient's needs. Ideally, the pump will operate within a pressure differential range of 20–40 mm Hg, and preferably at a pressure differential of 30 mm Hg. At least a portion of the blood flowing through the vein is drawn through the pump and oxygenator, thereby enhancing the effectiveness of the oxygenator in exchanging carbon dioxide for oxygen.

With the present arrangement, the maximum oxygen transfer to the blood is no longer limited by the blood flow rate generated solely by the patient as in prior art devices. Actively forcing the oxygen depleted blood through the oxygenator enhances the performance of the oxygenator so that a greater population of patients can utilize the intravascular lung technology. For example, patients who suffer from both lung ailments and who have reduced blood flow as a result of heart problems can utilize this system.

Reasonable variation and modification are possible within the spirit of the foregoing specification and drawings without departing from the scope of the invention.

The embodiments for which an exclusive property or privilege is claimed are defined as follows:

1. An active intravascular lung assist device configured for insertion into a cavity of a patient through which blood flows, said device comprising:

a gas exchanger adapted to deliver oxygen to blood flowing across the gas exchanger when positioned within the cavity;

a pump positioned adjacent the gas exchanger and adapted to receive blood therethrough, the pump creating a differential blood pressure across the gas exchanger thereby forcing blood through the exchanger and;

a catheter fluidly interconnecting the gas exchanger and the pump;

whereby the gas exchanger when positioned in the cavity can deliver oxygen to the blood independent of blood fluid flow generated by the patient's heart.

2. An active intravascular lung assist device according to claim 1 and further comprising a catheter fluidly interconnecting the gas exchanger and the pump.

3. An active intravascular lung assist device according to claim 2 wherein the cable extends through the gas exchanger and catheter to the pump.

4. An active intravascular lung assist device according to claim 1 wherein the gas exchanger has an inlet and an outlet, and the pump has an inlet and an outlet, the inlet of the pump being positioned adjacent the outlet of the gas exchanger so that the pump draws the blood through the exchanger.

5. An active intravascular lung assist device according to claim 4 wherein the pump is driven by a flexible drive cable that is adapted to extend extracorporeally when the pump and gas exchanger are positioned in the cavity.

6. An active intravascular lung assist device according to claim 5 wherein the cable extends through the gas exchanger to the pump.

7. An active intravascular lung assist device according to claim 1 wherein the gas exchanger has an inlet and an outlet, and the pump has an inlet and an outlet, the outlet of the pump being positioned adjacent the inlet of the gas exchanger so that the pump pushes the blood through the exchanger.

8. An active intravascular lung assist device according to claim 1 and further comprising a multi-lumen catheter having a proximal end mounted to the gas exchanger and a distal end mounted to a source of a first gas, the multi-lumen catheter being adapted to fluidly conduct a first gas therethrough in a first lumen, a second gas therethrough in a second lumen, and also adapted to receive therein at least a portion of the drive cable.

9. A method of oxygenating blood comprising the steps of:

providing a gas exchanger adapted to exchange oxygen for carbon dioxide as blood passes across the gas exchanger;

providing a pump which is fluidly interconnected to the gas exchanger;

percutaneously positioning the gas exchanger and pump within a blood flow conduit within a patient;

supplying oxygen to the gas exchanger; and driving the pump to force blood to flow across the gas exchanger.

10. A method of oxygenating blood according to claim 9 wherein the pump is positioned upstream from the gas exchanger so that the pump pushes blood through the gas exchanger.

11. A method of oxygenating blood according to claim 9 wherein the pump is positioned downstream from the gas exchanger so that the pump draws blood through the gas exchanger.

12. An active intravascular lung assist device configured for insertion into a cavity of a patient through which blood flows, said device comprising:

a gas exchanger adapted to deliver oxygen to blood flowing across the gas exchanger when positioned within the cavity;

a pump positioned adjacent the gas exchanger for creating a differential blood pressure across the gas exchanger thereby forcing blood through the exchanger; and a catheter fluidly interconnecting the gas exchanger and the pump;

whereby the gas exchanger when positioned in the cavity can deliver oxygen to the blood independent of blood fluid flow generated by the patient's heart.

13. An active intravascular lung assist device according to claim 12 wherein the pump is driven by a flexible drive cable that is adapted to extend extracorporeally when the pump and gas exchanger are positioned in the cavity.

14. An active intravascular lung assist device according to claim 13 wherein the cable extends through the gas exchanger and catheter to the pump.

15. An active intravascular lung assist device configured for insertion into a cavity of a patient through which blood flows, said device comprising:

a gas exchanger adapted to deliver oxygen to blood flowing across the gas exchanger when positioned within the cavity, the gas exchanger including an inlet and an outlet; and a pump positioned adjacent the gas exchanger for creating a differential blood pressure across the gas exchanger thereby forcing blood through the exchanger, the pump including an inlet and an outlet, the inlet of the pump being positioned adjacent the outlet of the gas exchanger so that the pump draws the blood through the exchanger;

whereby the gas exchanger when positioned in the cavity can deliver oxygen to the blood independent of blood fluid flow generated by the patient's heart.

16. An active intravascular lung assist device according to claim 15 and further comprising a catheter fluidly interconnecting the gas exchanger and the pump.

17. An active intravascular lung assist device according to claim 15 wherein the pump is driven by a flexible drive cable that is adapted to extend extracorporeally when the pump and gas exchanger are positioned in the cavity.

18. An active intravascular lung assist device according to claim 17 wherein the cable extends through the gas exchanger to the pump.

19. An active intravascular lung assist device configured for insertion into a cavity of a patient through which blood flows, said device comprising:

a gas exchanger adapted to deliver oxygen to blood flowing across the gas exchanger when positioned within the cavity, the gas exchanger including an inlet and an outlet; and a pump positioned adjacent the gas exchanger for creating a differential blood pressure across the gas exchanger thereby forcing blood through the exchanger, the pump including an inlet and an outlet, the outlet of the pump being positioned adjacent the inlet of the gas exchanger so that the pump pushes the blood through the exchanger;

a catheter fluidly interconnecting the gas exchanger and the pump;

whereby the gas exchanger when positioned in the cavity can deliver oxygen to the blood independent of blood fluid flow generated by the patient's heart.

20. An active intravascular lung assist device configured for insertion into a cavity of a patient through which blood flows, said device comprising:

a gas exchanger adapted to deliver oxygen to blood flowing across the gas exchanger when positioned within the cavity; and a pump positioned adjacent the gas exchanger for creating a differential blood pressure across the gas exchanger thereby forcing blood through the exchanger;

whereby the gas exchanger when positioned in the cavity can deliver oxygen to the blood independent of blood fluid flow generated by the patient's heart, and wherein the pump is driven by a flexible drive cable that is adapted to extend extracorporeally when the pump and gas exchanger are positioned in the cavity.

21. An active intravascular lung assist device according to claim 20 and further comprising a multi-lumen catheter having a proximal end mounted to the gas exchanger and a distal end mounted to a source of a first gas, the multi-lumen catheter being adapted to fluidly conduct a first gas therethrough in a first lumen, a second gas therethrough in a second lumen, and also adapted to receive therein at least a portion of the drive cable.

* * * * *